United States Patent
Mastri

(10) Patent No.: US 9,801,656 B2
(45) Date of Patent: Oct. 31, 2017

(54) SELF-ADJUSTING PNEUMATICALLY SEALED TROCAR

(71) Applicant: SurgiQuest, Inc., Milford, CT (US)

(72) Inventor: Dominick Mastri, Bridgeport, CT (US)

(73) Assignee: Surgiquest, Inc., Milford, CT (US)

( * ) Notice: Subject to any disclaimer, the term of this patent is extended or adjusted under 35 U.S.C. 154(b) by 36 days.

(21) Appl. No.: 15/000,549

(22) Filed: Jan. 19, 2016

(65) Prior Publication Data

US 2016/0220271 A1   Aug. 4, 2016

Related U.S. Application Data

(60) Provisional application No. 62/110,084, filed on Jan. 30, 2015.

(51) Int. Cl.
*A61M 13/00* (2006.01)
*A61B 17/34* (2006.01)
*A61B 17/02* (2006.01)
*A61B 17/00* (2006.01)

(52) U.S. Cl.
CPC ...... *A61B 17/3423* (2013.01); *A61B 17/0218* (2013.01); *A61B 17/3431* (2013.01); *A61B 17/3474* (2013.01); *A61M 13/003* (2013.01); *A61B 2017/00557* (2013.01); *A61B 2017/3419* (2013.01); *A61B 2017/3443* (2013.01); *A61B 2017/3484* (2013.01); *A61B 2017/3488* (2013.01); *A61M 2205/3344* (2013.01)

(58) Field of Classification Search
CPC .................................................. A61B 17/3474
See application file for complete search history.

(56) References Cited

U.S. PATENT DOCUMENTS

| | | |
|---|---|---|
| 7,798,998 B2 | 9/2010 | Thompson et al. |
| 7,806,870 B2 | 10/2010 | Mastri et al. |
| 7,854,724 B2 | 12/2010 | Stearns et al. |
| 8,216,189 B2 | 7/2012 | Stubbs et al. |
| 8,317,815 B2 | 11/2012 | Mastri et al. |

(Continued)

FOREIGN PATENT DOCUMENTS

WO   WO-2010042913 A2   4/2010

OTHER PUBLICATIONS

International Search Report and Written Opinion dated May 24, 2016 in connection with PCT/US2016/014023.

*Primary Examiner* — Jan Christopher Merene
(74) *Attorney, Agent, or Firm* — Locke Lord LLP; Scott D. Wofsy

(57) ABSTRACT

A surgical access device including a housing having a nozzle assembly, a gas supply plenum, a gas return plenum, and a pressure sensing plenum, as well as an elongated tubular body that extends from the housing portion and defines a central lumen communicating with the nozzle assembly and the gas return plenum, a telescopic cannula assembly associated with the tubular body and including a proximal section arranged coaxially within the tubular body and a distal section coaxially supported within the proximal section and mounted for movement relative to the proximal section between retracted and extended positions, and an elastomeric sheath associated with the telescopic cannula assembly and having a distal anchor portion for securing the surgical access device during a laparoscopic surgical procedure.

25 Claims, 7 Drawing Sheets

(56) References Cited

U.S. PATENT DOCUMENTS

| | | |
|---|---|---|
| 8,795,223 B2 | 8/2014 | Stearns et al. |
| 2007/0088274 A1* | 4/2007 | Stubbs ............... A61B 17/3421 |
| | | 604/164.01 |
| 2007/0088275 A1* | 4/2007 | Stearns ................ A61M 1/28 |
| | | 604/164.01 |
| 2008/0086080 A1 | 4/2008 | Mastri et al. |
| 2009/0182279 A1 | 7/2009 | Wenchell et al. |
| 2012/0245511 A1 | 9/2012 | Stearns et al. |
| 2014/0088491 A1* | 3/2014 | Azarbarzin ........ A61B 17/3421 |
| | | 604/26 |
| 2017/0007295 A1* | 1/2017 | Geisz ................. A61M 13/003 |

* cited by examiner

SELF-ADJUSTING PNEUMATICALLY SEALED TROCAR

CROSS-REFERENCE TO RELATED APPLICATIONS

The subject invention claims the benefit of priority from U.S. Provisional Patent Application 62/110,084 filed Jan. 30, 2015, the disclosure of which is herein incorporated by reference in its entirety.

BACKGROUND OF THE INVENTION

1. Field of the Invention

The subject invention is directed to laparoscopic surgery, and more particularly, to a self-adjusting pneumatically sealed trocar for use with an insufflation and gas recirculation system used during laparoscopic surgical procedures.

2. Description of Related Art

Laparoscopic or "minimally invasive" surgical techniques are becoming commonplace in the performance of procedures such as cholecystectomies, appendectomies, hernia repair and nephrectomies. Benefits of such procedures include reduced trauma to the patient, reduced opportunity for infection, and decreased recovery time. Such procedures within the abdominal (peritoneal) cavity are typically performed through a device known as a trocar or cannula, which facilitates the introduction of laparoscopic instruments into the abdominal cavity of a patient.

Additionally, such procedures commonly involve filling or "insufflating" the abdominal (peritoneal) cavity with a pressurized fluid, such as carbon dioxide, to create what is referred to as a pneumoperitoneum. The insufflation can be carried out by a surgical access device (sometimes referred to as a "cannula" or "trocar") equipped to deliver insufflation fluid, or by a separate insufflation device, such as an insufflation (veress) needle. Introduction of surgical instruments into the pneumoperitoneum without a substantial loss of insufflation gas is desirable, in order to maintain the pneumoperitoneum.

During typical laparoscopic procedures, a surgeon makes three to four small incisions, usually no larger than about twelve millimeters each, which are typically made with the surgical access devices themselves, typically using a separate inserter or obturator placed therein. Following insertion, the inserter is removed, and the trocar allows access for instruments to be inserted into the abdominal cavity. Typical trocars often provide means to insufflate the abdominal cavity, so that the surgeon has an open interior space in which to work.

The trocar must provide a means to maintain the pressure within the cavity by sealing between the trocar and the surgical instrument being used, while still allowing at least a minimum freedom of movement of the surgical instruments. Such instruments can include, for example, scissors, grasping instruments, and occluding instruments, cauterizing units, cameras, light sources and other surgical instruments. Sealing elements or mechanisms are typically provided on trocars to prevent the escape of insufflation gas. Sealing elements or mechanisms typically include a duckbill-type valve made of a relatively pliable material, to seal around an outer surface of surgical instruments passing through the trocar.

SurgiQuest, Inc., Milford, Conn. USA has developed surgical access devices that permit access to an insufflated surgical cavity without conventional mechanical seals, as described in whole or in part in commonly assigned U.S. Pat. No. 7,854,724 and U.S. Pat. No. 8,795,223, the disclosures of which are both incorporated herein by reference in their entireties.

Trocars for laparoscopic surgery are not typically provided with a facility for anchoring to the abdominal wall, and therefore can be accidentally removed therefrom during a procedure. Although some solutions to that problem have been developed, such a means for securing a trocar housing with suture anchors, such devices have been unreliable, cause unnecessary tissue trauma and can be expensive to manufacture.

A novel solution is disclosed in commonly assigned U.S. Pat. No. 7,806,870, the disclosure of which is incorporated herein by reference in its entirety. In the '870 patent, a surgical access device is described that includes a deformable elastomeric outer sheath that anchors the device to the abdominal wall from within the abdominal cavity.

There remains, however, a need in the art for a surgical access device that does not utilize conventional mechanical seals to prevent the escape of insufflating gas from the abdominal cavity, while also having an effective anchoring system to secure the device to the abdominal wall of a patient in an atraumatic manner that prevents accidental removal of the device during a surgical procedure. The present invention provides a novel solution.

SUMMARY OF THE INVENTION

The subject invention is directed to a new and useful surgical access device for use in laparoscopic procedures. The device comprises a proximal housing portion including an annular nozzle assembly, a gas supply plenum communicating with an upstream side of the annular nozzle assembly, a gas return plenum communicating with a downstream side of the annular nozzle assembly, and a pressure sensing plenum isolated from the annular nozzle assembly, the gas supply plenum and the gas return plenum. An elongated tubular body portion extends distally from the proximal housing portion and defines a central lumen that communicates with the downstream side of the annular nozzle assembly and with the gas return plenum.

A telescopic cannula assembly is operatively associated with the elongated tubular body portion and includes a proximal section arranged coaxially within the tubular body portion and a distal section coaxially supported within the proximal section. The distal section is mounted for movement with respect to the proximal section between a retracted position and an extended position.

An elastomeric sheath is operatively associated with the telescopic cannula assembly. The sheath has a radially enlarged distal anchor portion for securing the surgical access device with respect to the abdominal wall of a patient during a laparoscopic surgical procedure when the distal section of the telescopic cannula assembly is in the retracted position.

A proximal end of the elastomeric sheath is secured to the housing portion and a distal end of the elastomeric sheath is secured to the distal section of the telescopic cannula assembly. Preferably, the proximal end of the elastomeric sheath is secured between a bottom edge of the housing portion an complimentary end cap. The elastomeric sheath is adapted and configured to stretch in elongated manner when the distal section of the telescopic cannula assembly is moved from the retracted position to the extended position, such that an outer diameter of the radially enlarged distal anchor portion of the elastomeric sheath is reduced.

The pressure sensing plenum is in fluid communication with a pressure sensing and insufflation pathway formed within the tubular body portion. The pressure sensing and insufflation pathway extends between an inner wall of the tubular body portion and an outer wall of the proximal section of the telescoping cannula assembly. The pressure sensing and insufflation pathway further extends between an outer wall of the distal section of the telescopic cannula assembly and an inner wall of the elastomeric sheath. The pressure sensing and insufflation pathway is defined at least in part by a plurality of circumferentially spaced apart radially outwardly projecting ribs formed on the outer wall of the distal section of the telescopic cannula assembly. The pressure sensing and insufflation pathway communicates with a central lumen of the distal section of the telescoping cannula assembly through a plurality of apertures formed in the distal end portion thereof.

The housing portion includes a connective fitting defining a first passage to facilitate fluid communication between a source of pressurized gas and the gas supply plenum. The housing portion includes a connective fitting defining a second passage to facilitate fluid communication between a source of vacuum and the gas return plenum. The housing portion includes a connective fitting defining a third passage to facilitate fluid communication between a source of insufflation gas and the pressure sensing plenum. The housing portion includes a connective fitting defining a third passage to facilitate fluid communication between a pressure sensor and the pressure sensing plenum.

Preferably, means are associated with the distal section of the telescopic cannula assembly for engaging an obturator shaft extended through the central lumen to effectuate movement of the distal section of the telescopic cannula between the retracted position and the extended position.

The annular nozzle assembly includes a plurality of jets that are dimensioned and configured to accelerate pressurized gas delivered to the gas supply plenum to generate a continuous pressure barrier within the central lumen of the tubular body portion that inhibits egress of insufflation gas from the abdominal cavity of a patient. The annular nozzle assembly includes a cylindrical jet set having a pair of axially spaced apart outer sealing rings for sealingly isolating the nozzle assembly within the proximal housing portion. The gas return plenum includes a plurality of circumferentially disposed spaced apart axial fins distal to the cylindrical jet set for directing gas flow.

The subject invention is also directed to a surgical access device for use in laparoscopic procedures that comprises a proximal housing portion, an elongated tubular body portion extending distally from the proximal housing portion and defining a central lumen, a telescopic cannula assembly operatively associated with the elongated tubular body portion and including a proximal section arranged coaxially within the tubular body portion and a distal section coaxially supported within the proximal section and mounted for movement with respect to the proximal section between a retracted position and an extended position.

The device further comprises an elastomeric sheath operatively associated with the telescopic cannula assembly and having a radially enlarged distal anchor portion for securing the surgical access device with respect to the abdominal wall of a patient during a laparoscopic surgical procedure when the distal section of the telescopic cannula assembly is in the retracted position, wherein the elastomeric sheath is adapted and configured to stretch in elongated manner when the distal section of the telescopic cannula assembly is moved from the retracted position to the extended position, such that an outer diameter of the radially enlarged distal anchor portion of the elastomeric sheath is reduced.

These and other features of the self-adjusting pneumatically sealed trocar of the subject invention and the manner in which it is manufactured and employed will become more readily apparent to those having ordinary skill in the art from the following enabling description of the preferred embodiments of the subject invention taken in conjunction with the several drawings described below.

BRIEF DESCRIPTION OF THE DRAWINGS

So that those skilled in the art to which the subject invention appertains will readily understand how to make and use the self-adjusting pneumatically sealed trocar of the subject invention without undue experimentation, preferred embodiments thereof will be described in detail herein below with reference to certain figures, wherein.

DETAILED DESCRIPTION OF PREFERRED EMBODIMENTS

Figure 1:
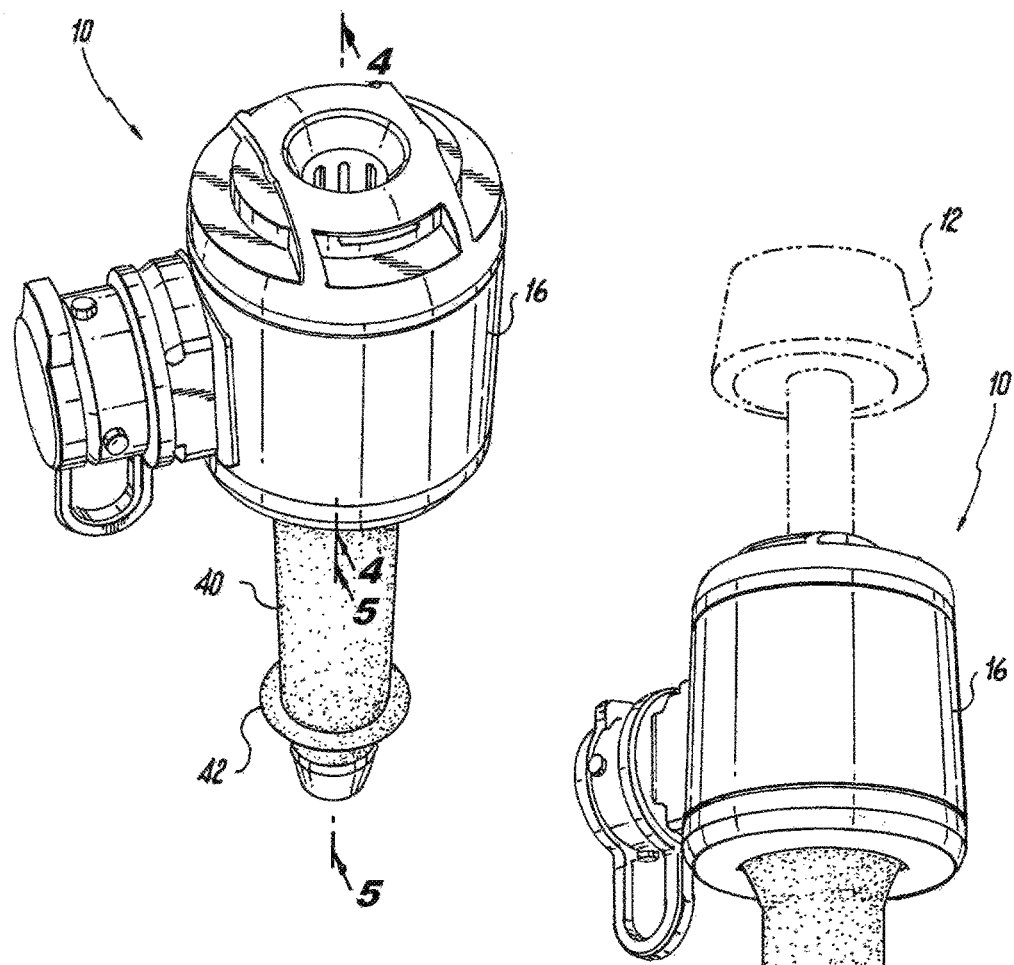
FIG. 1 is a perspective view of the surgical access device of the subject invention as viewed from above.

Referring now to the drawings, wherein like reference numerals identify similar structural features or aspects of the subject invention, there is illustrated in FIG. 1 a surgical access device constructed in accordance with a preferred embodiment of the subject invention and designated generally by reference numeral 10. Surgical access device 10 is adapted and configure for use during laparoscopic surgical procedures in conjunction with an obturator 12 having a sharpened tip 14 for piercing through the abdominal all of a patient to gain access to the patient's abdominal cavity.

Exemplary obturator tips are disclosed in commonly assigned U.S. Pat. No. 8,317,815, the disclosure of which is incorporated herein by reference in its entirety.

Figure 3:
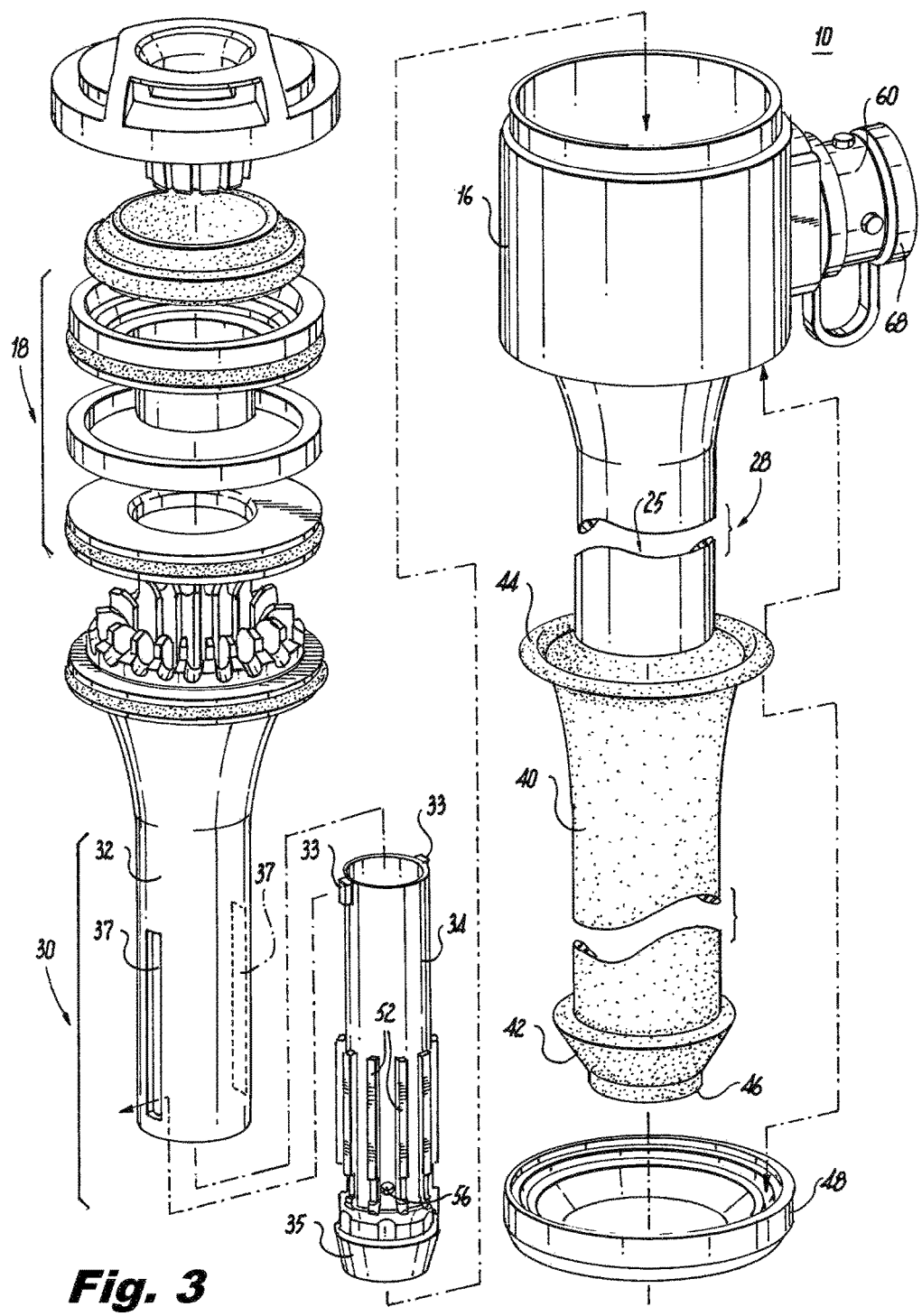
FIG. 3 is an exploded perspective view of the surgical access device of the subject invention with parts separated for ease of illustration.
Figure 4:
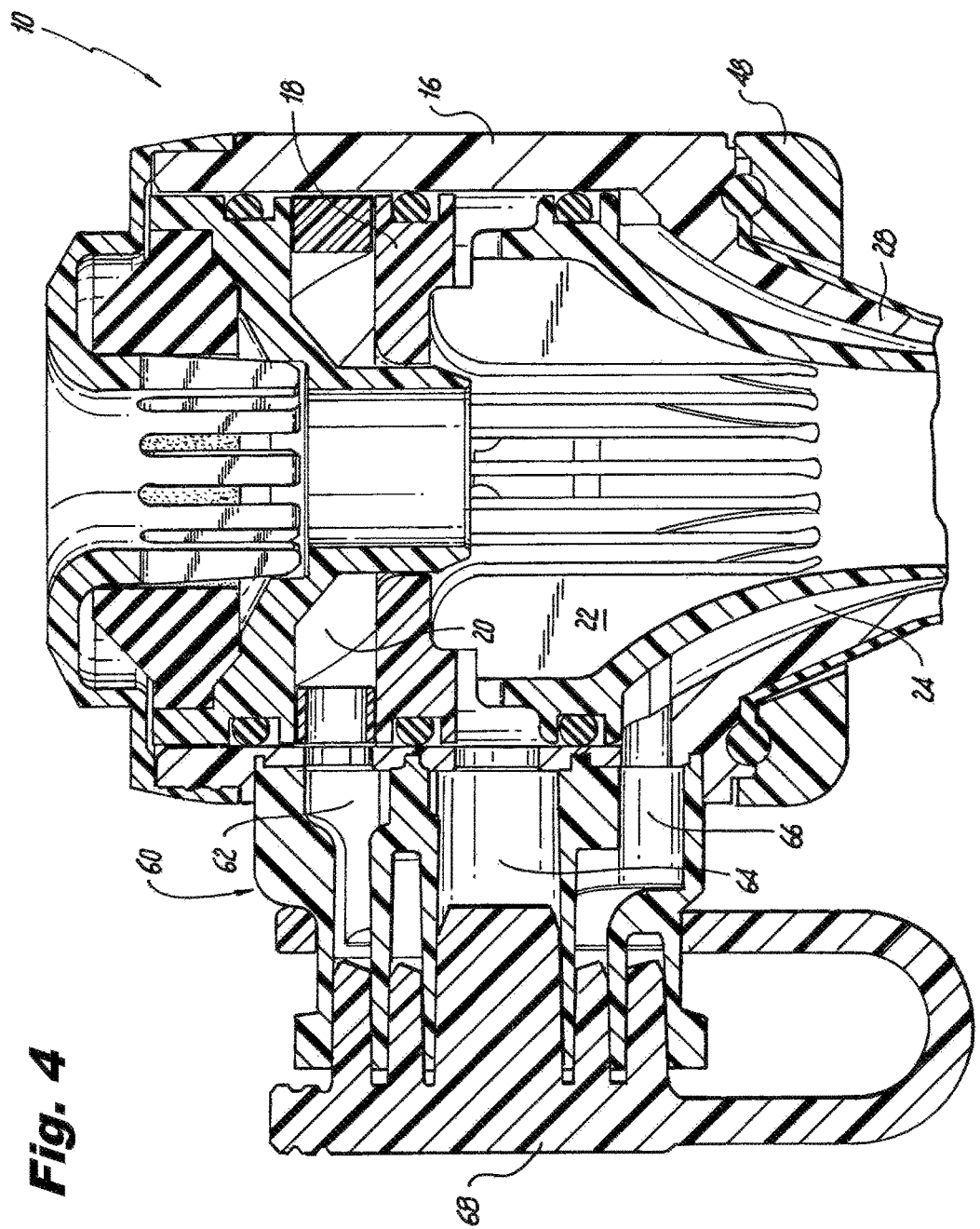
FIG. 4 is a cross-sectional view of the housing portion of the surgical access device of the subject invention taken along line 4-4 of FIG. 1, illustrating internal features of the housing portion including the nozzle assembly which generates a continuous pressure barrier within the central lumen of the tubular body portion that inhibits egress of insufflation gas from the abdominal cavity of a patient.

Referring to FIGS. 3 and 4, the surgical access device 10 includes a proximal housing portion 16 containing an annular nozzle assembly 18. The nozzle assembly 18 is described in greater detail in commonly assigned U.S. Pat. No. 8,795,223, which is incorporated herein by reference in its entirety.

A gas supply plenum 20 communicating with an upstream side of the annular nozzle assembly 18, a gas return plenum 22 communicating with a downstream side of the annular nozzle assembly 18, and a pressure sensing/insufflating plenum 24 isolated from the annular nozzle assembly 18, the gas supply plenum 20 and the gas return plenum 22. An elongated tubular body portion 28 extends distally from the proximal housing 16 portion and defines a central lumen 25 that communicates with the downstream side of the annular nozzle assembly 18 and with the gas return plenum 22.

Figure 7:
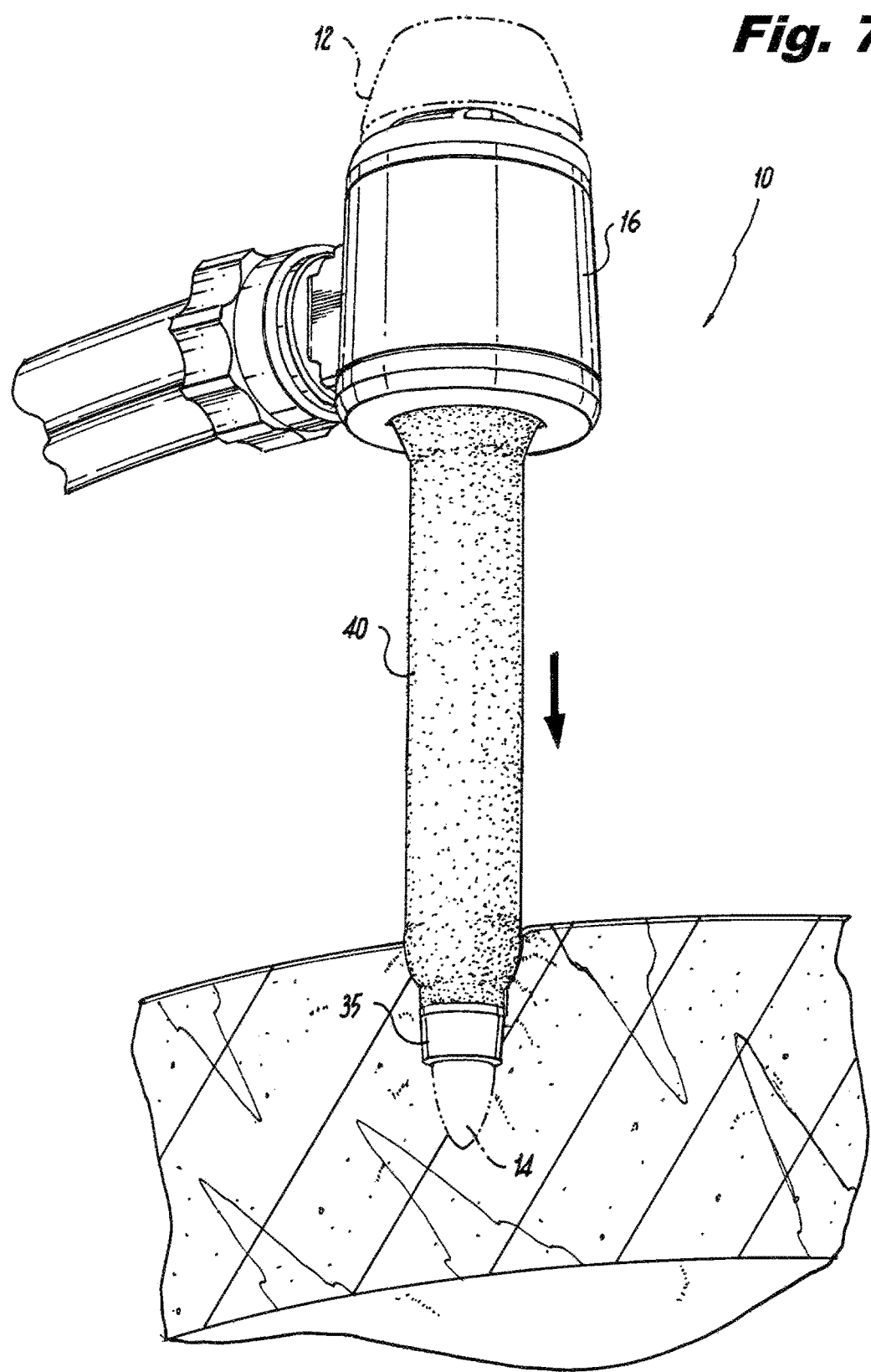
FIG. 7 is an illustration of the surgical access device of the subject invention, with the elastomeric sheath in a stretched condition so that the distal anchor portion is reduced in diameter for introduction through the abdominal wall of a patient.

A telescopic cannula assembly 30 is operatively associated with the elongated tubular body portion 28 and includes a proximal (outer) section 32 arranged coaxially within the tubular body portion 28 and a distal (inner) section 34 coaxially supported within the proximal section 28. The distal section 34 is mounted for guided movement with respect to the proximal section 28 between a retracted position (see FIG. 28) and an extended position (see FIG. 7). More particularly, the distal section 34 includes diametrically opposed radially outwardly projecting follower tabs 33 that are dimensioned and configured to travel within corresponding diametrically opposed elongated grooves 37 that are formed in the wall of the proximal section 32.

Figure 8:
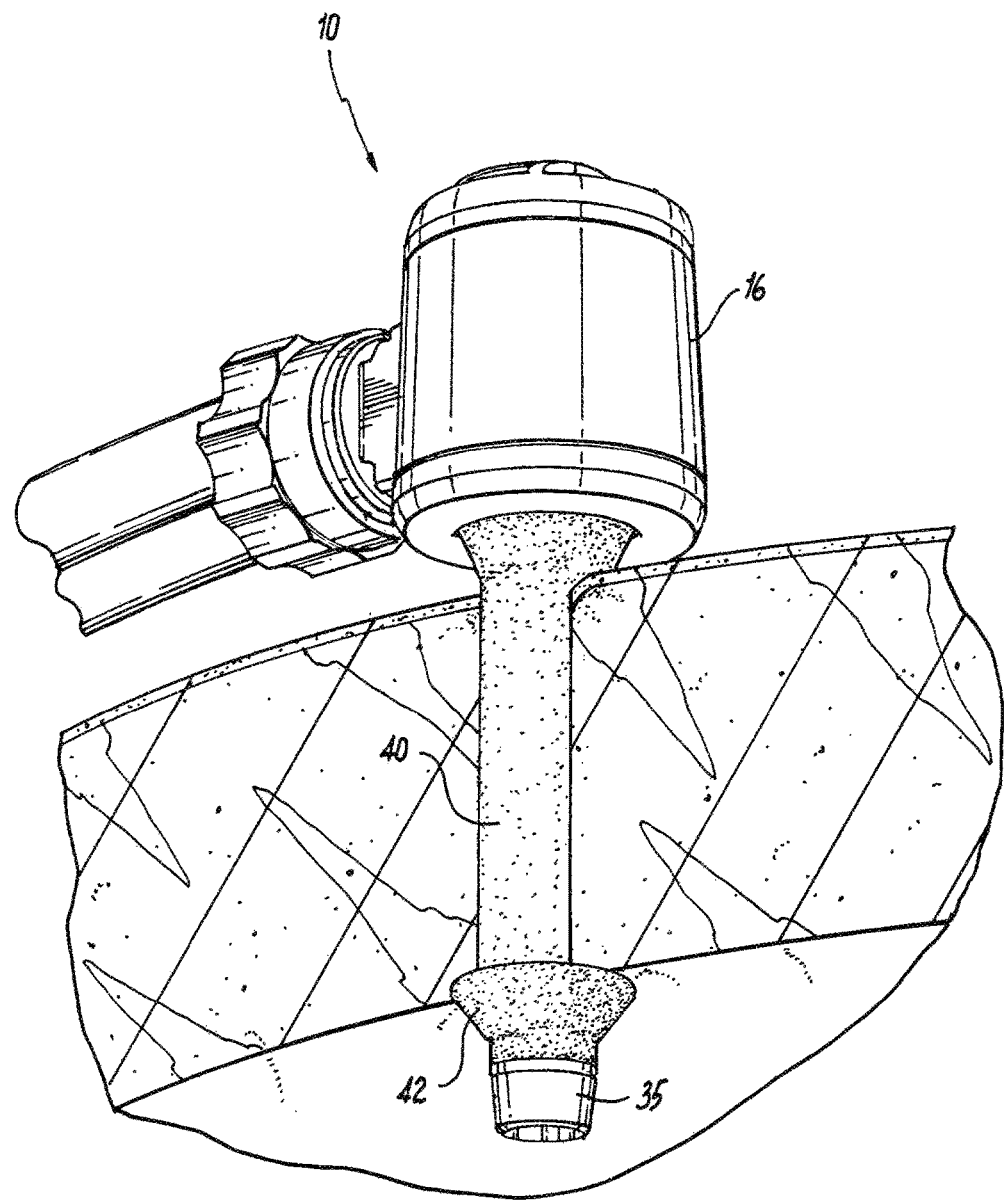
FIG. 8 is an illustration of the surgical access device of the subject invention, with the elastomeric sheath in an unstretched condition so that the distal anchor portion has a radially enlarged diameter for anchoring the surgical access device with respect to the abdominal wall of the patient.

An elastomeric sheath 40 is operatively associated with the telescopic cannula assembly 30. The sheath 40 has a radially enlarged distal anchor 42 portion for securing the surgical access device 10 with respect to the abdominal wall of a patient during a laparoscopic surgical procedure when the distal section 34 of the telescopic cannula assembly 30 is in the retracted position, as best seen in FIG. 8. The sheath 40 preferably has circumferential serrations formed on its outer surface, as shown for example in U.S. Pat. No. 7,806,870.

Figure 2:
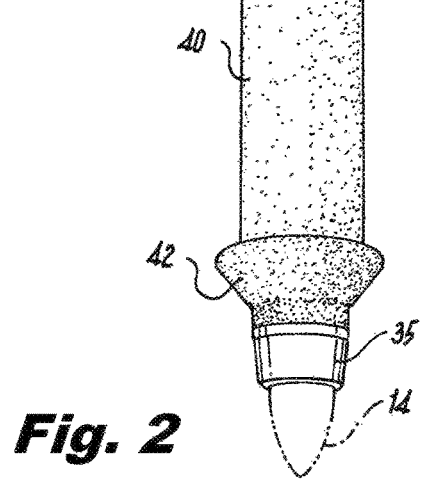
FIG. 2 is a perspective view of the surgical access device of the subject invention as viewed in elevation with an obturator shaft extended through a central lumen of the housing portion and tubular body portion of the device.

A proximal end 44 of the elastomeric sheath 40 is secured to the housing portion 16 and a distal end 44 of the elastomeric sheath 40 is secured to the distal end 35 of the distal section 34 of the telescopic cannula assembly 30. The proximal end 44 of the elastomeric sheath 40 is secured between a bottom edge of the housing portion 16 and a complimentary end cap 48. The elastomeric sheath 40 is adapted and configured to stretch in elongated manner when the distal section 34 of the telescopic cannula assembly 30 is moved from the retracted position of FIG. 2 to the extended position of FIG. 8, such that an outer diameter of the radially enlarged distal anchor portion 42 of the elastomeric sheath 40 is reduced. This is achieved using the obturator 12 as a stretching tool, as discussed in more detail below.

Figure 5:
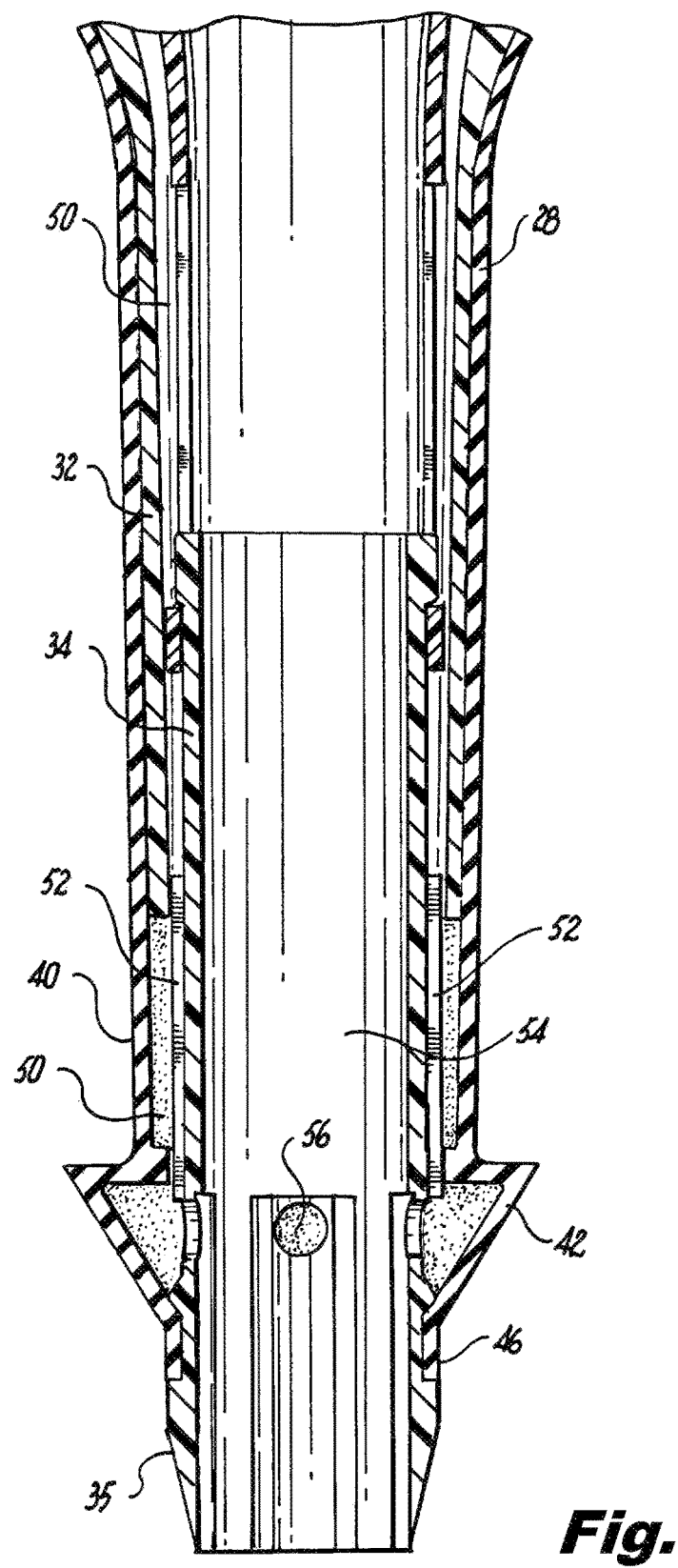
FIG. 5 is a cross-sectional view of the body portion of the surgical access device of the subject invention taken along line 5-5 of FIG. 1, illustrating internal features of the telescopic cannula assembly.

Referring to FIG. 5, the pressure sensing plenum 24 is in fluid communication with a pressure sensing and insufflation pathway 50 formed within the tubular body portion 28. The pressure sensing and insufflation pathway 50 extends between an inner wall of the tubular body portion 28 and an outer wall of the proximal (outer) section 32 of the telescoping cannula assembly 30. The pressure sensing and insufflation pathway 50 further extends between an outer wall of the distal (inner) section 34 of the telescopic cannula assembly 30 and an inner wall of the elastomeric sheath 40.

Figure 6:
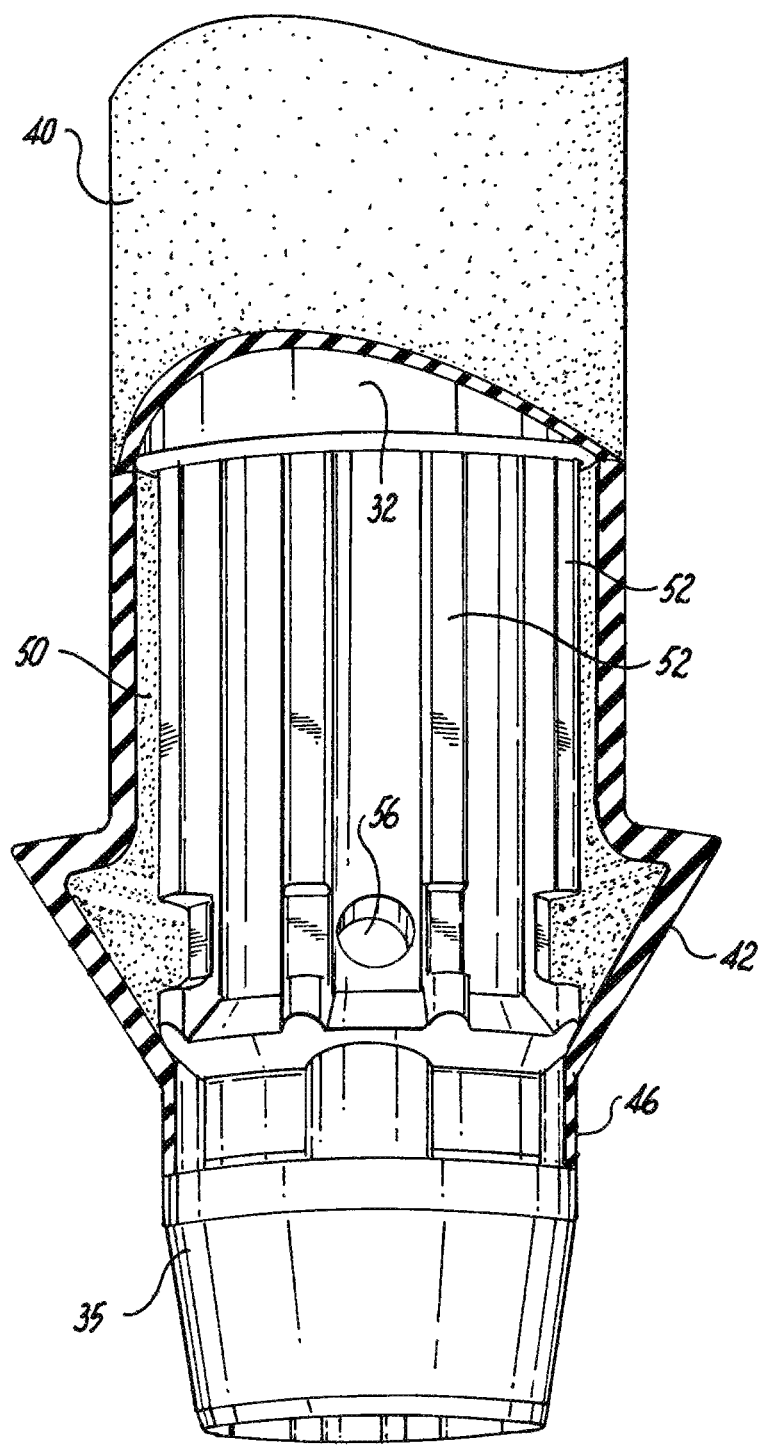
FIG. 6 is an enlarged localized view of the distal section of the body portion of the surgical access device of the subject invention, with the elastomeric sheath broken-away to illustrate internal features of the telescopic cannula assembly.

The pressure sensing and insufflation pathway 50 is defined at least in part by a plurality of circumferentially spaced apart radially outwardly projecting ribs 52 formed on the outer wall of the distal section 34 of the telescopic cannula assembly 30. The pressure sensing and insufflation pathway 50 communicates with a central lumen 54 of the distal section 34 of the telescoping cannula assembly 30 through a plurality of apertures 56 formed in the distal end portion thereof, as seen in FIG. 6.

Referring again to FIG. 4, the housing portion 16 includes a connective fitting 60 defining a first passage 62 to facilitate fluid communication between a source of pressurized gas and the gas supply plenum 20. The connective fitting 60 defines a second passage 64 to facilitate fluid communication between a source of vacuum and the gas return plenum 22. The connective fitting 60 further defines a third passage 66 to facilitate fluid communication between a source of insufflation gas and the pressure sensing/insufflation plenum 24.

Structure is provided within the distal section 34 of the telescopic cannula assembly 30 for engaging a surface feature of obturator shaft 12 extended through the central lumen to effectuate movement of the distal section 34 of the telescopic cannula assembly 30 between the retracted position and the extended position.

While the subject invention has been shown and described with reference to preferred embodiments, those skilled in the art will readily appreciate that various changes and/or modifications may be made thereto without departing from the spirit and scope of the subject invention as defined by the appended claims.

What is claimed is:

1. A surgical access device for use in laparoscopic procedures comprising:
   a) a proximal housing portion including an annular nozzle assembly, a gas supply plenum communicating with an upstream side of the annular nozzle assembly, a gas return plenum communicating with a downstream side of the annular nozzle assembly, and a pressure sensing plenum isolated from the annular nozzle assembly, the gas supply plenum and the gas return plenum;
   b) an elongated tubular body portion extending distally from the proximal housing portion and defining a central lumen communicating with the downstream side of the annular nozzle assembly and with the gas return plenum;
   c) a telescopic cannula assembly operatively associated with the elongated tubular body portion and including a proximal section arranged coaxially within the tubular body portion and a distal section coaxially supported within the proximal section and mounted for movement with respect to the proximal section between a retracted position and an extended position; and
   d) an elastomeric sheath operatively associated with the telescopic cannula assembly and having a radially enlarged distal anchor portion for securing the surgical access device with respect to the abdominal wall of a patient during a laparoscopic surgical procedure when the distal section of the telescopic cannula assembly is in the retracted position, wherein the pressure sensing plenum is in fluid communication with a pressure sensing and insufflation pathway formed within the tubular body portion, wherein the pressure sensing and insufflation pathway further extends between an outer wall of the distal section of the telescopic cannula assembly and an inner wall of the elastomeric sheath, and wherein the pressure sensing and insufflation pathway communicates with a central lumen of the distal section of the telescoping cannula assembly through a plurality of apertures formed in the distal end portion thereof.

2. A surgical access device as recited in claim 1, wherein a proximal end of the elastomeric sheath is secured to the housing portion and a distal end of the elastomeric sheath is secured to the distal section of the telescopic cannula assembly.

3. A surgical access device as recited in claim 2, wherein the proximal end of the elastomeric sheath is secured between a bottom edge of the housing portion an complimentary end cap.

4. A surgical access device as recited in claim 2, wherein the elastomeric sheath is adapted and configured to stretch in elongated manner when the distal section of the telescopic cannula assembly is moved from the retracted position to the extended position, such that an outer diameter of the radially enlarged distal anchor portion of the elastomeric sheath is reduced.

5. A surgical access device as recited in claim 1, wherein the pressure sensing and insufflation pathway extends between an inner wall of the tubular body portion and an outer wall of the proximal section of the telescoping cannula assembly.

6. A surgical access device as recited in claim 1, wherein the pressure sensing and insufflation pathway is defined in part by a plurality of circumferentially spaced apart radially outwardly projecting ribs formed on the outer wall of the distal section of the telescopic cannula assembly.

7. A surgical access device as recited in claim 1, wherein the housing portion includes a connective fitting defining a first passage to facilitate fluid communication between a source of pressurized gas and the gas supply plenum.

8. A surgical access device as recited in claim 1, wherein the housing portion includes a connective fitting defining a second passage to facilitate fluid communication between a source of vacuum and the gas return plenum.

9. A surgical access device as recited in claim 1, wherein the housing portion includes a connective fitting defining a third passage to facilitate fluid communication between a source of insufflation gas and the pressure sensing plenum.

10. A surgical access device as recited in claim 1, wherein the housing portion includes a connective fitting defining a third passage to facilitate fluid communication between a pressure sensor and the pressure sensing plenum.

11. A surgical access device as recited in claim 1, wherein means are associated with the distal section of the telescopic cannula assembly for engaging an obturator shaft extended through the central lumen to effectuate movement of the distal section of the telescopic cannula between the retracted position and the extended position.

12. A surgical access device as recited in claim 1, wherein the annular nozzle assembly includes a plurality of jets that are dimensioned and configured to accelerate pressurized gas delivered to the gas supply plenum to generate a continuous pressure barrier within the central lumen of the tubular body portion that inhibits egress of insufflation gas from the abdominal cavity of a patient.

13. A surgical access device as recited in claim 1, wherein the annular nozzle assembly includes a cylindrical jet set having a pair of axially spaced apart outer sealing rings for sealingly isolating the nozzle assembly within the proximal housing portion.

14. A surgical access device as recited in claim 1, wherein the gas return plenum includes a plurality of circumferentially disposed spaced apart axial fins distal to the cylindrical jet set for directing gas flow.

15. A surgical access device for use in laparoscopic procedures comprising:
 a) a proximal housing portion including an annular nozzle assembly, a gas supply plenum communicating with an upstream side of the annular nozzle assembly, a gas return plenum communicating with a downstream side of the annular nozzle assembly, and a pressure sensing plenum isolated from the annular nozzle assembly, the gas supply plenum and the gas return plenum;
 b) an elongated tubular body portion extending distally from the proximal housing portion and defining a central lumen;
 c) a telescopic cannula assembly operatively associated with the elongated tubular body portion and including a proximal section arranged coaxially within the tubular body portion and a distal section coaxially supported within the proximal section and mounted for movement with respect to the proximal section between a retracted position and an extended position;
 d) an elastomeric sheath operatively associated with the telescopic cannula assembly and having a radially enlarged distal anchor portion for securing the surgical access device with respect to the abdominal wall of a patient during a laparoscopic surgical procedure when the distal section of the telescopic cannula assembly is in the retracted position, wherein the elastomeric sheath is adapted and configured to stretch in elongated manner when the distal section of the telescopic cannula assembly is moved from the retracted position to the extended position, such that an outer diameter of the radially enlarged distal anchor portion of the elastomeric sheath is reduced wherein the pressure sensing and insufflation pathway extends between an inner wall of the tubular body portion and an outer wall of the proximal section of the telescoping cannula assembly, wherein the pressure sensing and insufflation pathway further extends between an outer wall of the distal section of the telescopic cannula assembly and an inner wall of the elastomeric sheath, and wherein the pressure sensing and insufflation pathway is defined in part by a plurality of circumferentially spaced apart radially outwardly projecting ribs formed on the outer wall of the distal section of the telescopic cannula assembly.

16. A surgical access device as recited in claim 15, further comprising means formed within a central lumen of the distal section of the telescopic cannula assembly for engaging an obturator shaft extended therethrough to effectuate movement of the distal section of the telescopic cannula assembly between the retracted position and the extended position.

17. A surgical access device as recited in claim 15, wherein a proximal end of the elastomeric sheath is secured to the housing portion and a distal end of the elastomeric sheath is secured to the distal section of the telescopic cannula assembly.

18. A surgical access device as recited in claim 17, wherein the proximal end of the elastomeric sheath is secured between a bottom edge of the housing portion an complimentary end cap.

19. A surgical access device as recited in claim 15, wherein the central lumen of the tubular body portion is in communication with the downstream side of the annular nozzle assembly and with the gas return plenum.

20. A surgical access device as recited in claim 15, wherein the pressure sensing plenum is in fluid communication with a pressure sensing and insufflation pathway formed within the tubular body portion.

21. A surgical access device as recited in claim 15, wherein the pressure sensing and insufflation pathway communicates with a central lumen of the distal section of the telescoping cannula assembly through a plurality of apertures formed in the distal end portion thereof.

22. A surgical access device as recited in claim 15, wherein the housing portion includes a connective fitting defining a first passage to facilitate fluid communication between a source of pressurized gas and the gas supply plenum.

23. A surgical access device as recited in claim 15, wherein the housing portion includes a connective fitting defining a second passage to facilitate fluid communication between a source of vacuum and the gas return plenum.

24. A surgical access device as recited in claim 15, wherein the housing portion includes a connective fitting defining a third passage to facilitate fluid communication between a source of insufflation gas and the pressure sensing plenum.

25. A surgical access device as recited in claim 15, wherein the housing portion includes a connective fitting defining a third passage to facilitate fluid communication between a pressure sensor and the pressure sensing plenum.

* * * * *